United States Patent [19]

Grace

[11] Patent Number: 5,651,781
[45] Date of Patent: Jul. 29, 1997

[54] SURGICAL CUTTING INSTRUMENT

[75] Inventor: Kenneth P. Grace, Woodland Park, Colo.

[73] Assignee: Grace-Wells Technology Partners No. 1, L.P., Woodland Park, Colo.

[21] Appl. No.: 425,100

[22] Filed: Apr. 20, 1995

[51] Int. Cl.⁶ .................................................. A61B 17/32
[52] U.S. Cl. ........................... 606/1; 606/170; 606/171; 606/180
[58] Field of Search ..................... 606/108, 170–1, 606/1, 167, 180, 185, 127

[56] References Cited

U.S. PATENT DOCUMENTS

| | | | |
|---|---|---|---|
| 4,582,056 | 4/1986 | McCorkle, Jr. | 606/1 |
| 4,729,763 | 3/1988 | Henrie | 606/22 |
| 4,923,462 | 5/1990 | Stevens | 606/180 |
| 5,152,744 | 10/1992 | Krause et al. | 606/180 |

*Primary Examiner*—Robert A. Hafer
*Assistant Examiner*—Benjamin Koo
*Attorney, Agent, or Firm*—Davis, Graham & Stubbs LLP

[57] ABSTRACT

A surgical cutting instrument for removing objects, such as a pacemaker lead or catheter, embedded in biological tissue. The cutting instrument includes a rigid proximal end and a flexible distal end, the flexible distal end having circular opening and a cutting blade disposed longitudinally therein. A control handle connected to the rigid proximal end and extending radially therefrom provides a force applied to an inner member which extends the cutting blade beyond the circular opening and simultaneously rotates the cutting blade to cut tissue exposed to the blade.

9 Claims, 2 Drawing Sheets

SURGICAL CUTTING INSTRUMENT

FIELD OF THE INVENTION

This invention relates to a mechanical apparatus for extracting an elongated object, such as a pacemaker lead or catheter, embedded in biological tissue.

BACKGROUND OF THE INVENTION

Pacemakers are devices that are surgically implanted in the chests of patients to maintain the heart beat at a regular rate. Pacemaker leads are the elongated wires that connect the pacemaker to the heart. The leads are ordinarily comprised of an insulated wire coil terminating with an electrode and are typically passed through the venous system before entering the heart via the superior vena cava. The pacemaker lead electrodes are anchored to the wall of the heart chamber, such as the right ventricle or right atrium, and deliver pacemaker pulse generator charges to the heart muscle and conduct cardiac signals back to the sensing circuit of the pulse generator. Although endocardial pacemaker lead implantation is considered to be a relatively routine procedure, pacemaker lead explantation is still a rather complicated, time-consuming procedure and is associated with significant risk.

The difficulty and risks associated with endocardial pacemaker lead explantation are due to the formation of fibrocollagenous scar tissue adhesions that encase the lead coil to the walls of the veins to the heart and encapsulate the lead electrode in the heart chamber. The longer the pacemaker leads reside within the vasculature and heart chamber, the greater the risks and difficulty of explantation.

Because of the significant risk, pacing leads are typically only removed when life-threatening conditions exist, or to prevent a potentially life-threatening situation from occurring. Mandatory conditions for pacing lead removal include the presence of septicemia (proliferation of infectious agents, such as bacteria and their toxins, in the blood) or endocarditis (inflammation of the inner lining of the heart due to infection).

Pacemaker leads can also fail, necessitating replacement, or no longer be required. Reasons for failure include lead fracture, insulation deterioration, or an increase in electrode resistance, thereby impeding the passage of the signals between the pacemaker and the heart. Migration of severed endocardial leads, causing mechanically induced ventricular arrhythmia, and protrusion of lead coil wires from the insulation are also considered mandatory conditions for lead removal. However, in many instances the risk of removing failed or unused pacemaker leads, using current methods, is greater than the risk of leaving them in place. In these situations, they are usually capped off and left anchored to the wall of the heart chamber.

Unfortunately, there are substantial risks associated with leaving failed and unused leads in place. The risks of leaving these leads in place include an increased likelihood of infection or blood clot formation around the old and entangled pacing leads. Other complications associated with leaving failed and unused leads in place are that the leads can restrict the operation of the heart valves and hinder the implantation of new leads in the heart. Thus, it is preferable to remove unused and failed leads whenever possible.

There are currently three principal techniques for endocardial pacemaker lead explantation. These techniques include traction, the combined use of traction and countertraction, and cardiac surgery.

With traction, the pacemaker lead is pulled directly or with the aid of a snare or catheter. U.S. Pat. No. 4,574,800, of Peers-Traverton, describes a device for applying traction to a pacing lead. The drawbacks of this technique include the fact that the procedure involves significant risk and is oftentimes unsuccessful. Associated complications include arrhythmias (irregular heart beat), low blood pressure, the inward pulling of the heart wall towards the heart valve, or even rupture of the heart wall. In addition, the pulling force may cause the pacemaker lead to be distorted or broken, impeding the ability to use other transvenous techniques. If the lead is severed, surgical removal is required.

The use of traction combined with countertraction has been shown to be less hazardous than traction alone but the technique is complicated and procedure success is highly dependent on the skill and experience of the physician. This method is also associated with relatively high complication rates. The technique most often practiced involves the use of a locking stylet, which is a wire that is advanced through the lumen of the pacing lead coil until it reaches the distal portion of the lead. The distal tip of the wire is configured with a fine wire coil that is wound clockwise so that when the stylet wire is rotated counterclockwise, the distal tip locks into the lead coil. The proximal end of the stylet can be shaped into a loop to act as a handle when applying traction. The purpose of the locking stylet is to provide stiffness and tensile strength to the pacing lead coil and deliver traction force directly to the distal tip of the lead. Once the locking stylet is in place, countertraction is applied by advancing one, or more commonly two, stainless steel, PTFE, or polypropylene sheaths over the stylet/pacing lead coil. When two sheaths are used, they are advanced in a telescoping fashion with one inside the other. The telescoping sheaths are passed over the pacemaker lead and when scar tissue is encountered, the sheaths are manually pushed, generally with substantial force, through the scar tissue adhesions by dilating, tearing and sliding over the tissue. Once the distal tips of the telescoping sheaths reach an area close to the electrode in the heart chamber, the electrode is freed from the fibrous cap in the chamber by pulling on the locking stylet.

The traction/countertraction method is a complex procedure and is highly dependent on physician skill and experience. Two critical aspects are 1) how hard to pull on the locking stylet, and 2) how hard to push the telescoping sheaths. Applying too much pulling or pushing force increases the risk of tearing the vein or heart chamber, or damaging the pacing lead wire. If the lead is severed, surgical removal is required.

Much of the procedure complexity is attributed to the complexity of the devices currently used to apply traction and countertraction. For example, U.S. Pat. Nos. 4,471,777, 4,582,056 and 4,576,162, all of McCorkle, describe a composite assembly of three catheters and method for endovascular lead extraction. The three catheter assembly includes a tool for applying tensile force to the electrode lead (the grasping catheter) and two catheters, one positioned over the other, with outward facing sharp serrations for separating scar tissue from the pacing lead and electrode. U.S. Pat. Nos. 4,943,289, 4,988,347, 5,011,482, 5,013,310, and 5,207,683, all of Goode et al., describe a stylet wire that attaches to the pacemaker electrode and separator tube, comprised of a hollow tube made of semi-rigid material, for separating the pacemaker lead from the vessel wall.

The third commonly practiced pacemaker lead extraction method is surgical removal. Surgery is also associated with significant risk and high cost. Additionally, not all patients, such as ill and elderly patients, are surgical candidates.

Another method, although still being investigated and therefore not widely practiced, involves the application of laser energy to separate pacemaker leads from scar adhesions. Theoretically, the cutting action of the laser reduces the amount of mechanical force required to separate the pacemaker lead from the vascular structure, thereby reducing the potential for rupturing the vessel or heart chamber wall. The main drawback of this method, however, is that it requires the use of highly complex and expensive laser technology.

Many surgical instruments exist with various cutting blade designs and mechanisms for separating objects from biological tissues. However, none of these instrument designs are appropriate for the removal of an elongated object, such as a pacemaker lead. For example, a variety of rigid mechanical cutting instruments are known for various other surgical applications, such as U.S. Pat. Nos. 4,461,305 of Cibley, 5,047,008 of de Juan et al., 4,306,570 of Matthews, 5,324,300 of Elias et al., 5,112,299 of Pascaloff, 5,275,609 and 5,290,303 of Pingleton et al. Since these devices are not flexible, their application is limited to straight passageways. Different flexible cutting instruments are described by U.S. Pat. Nos. 4,729,763 of Henrie, 4,754,755 of Husted, and 5,152,744 of Krause et al. U.S. Pat. No. 4,729,763 of Henrie describes a catheter comprised preferably of steel wire with a blade tip that is rotated using a motor drive, and U.S. Pat. No. 5,152,744 of Krause et al. describes a flexible instrument with rigid proximal and distal ends. The flexibility of this device is achieved by cutting grooves or holes into the tube. U.S. Pat. No. 4,646,738, of Trott, describes a rotatable surgical tool containing a tubular flexible coupler, comprised of a plurality of coaxial spirally wound layers for transmitting rotational movement. None of these mechanical cutting instruments, whether flexible or rigid, utilize a metal bellows for flexibility, trackability, blade extension, or torque transfer to the distal blade. Additionally, none of the instruments involve a cutting mechanism comprised of concurrent blade extension and rotation.

To overcome the problems encountered with removal of pacemaker leads from the heart, it is necessary to use an instrument that provides precise, controlled cutting. The instrument should be capable of precise placement of the blade before cutting takes place. The extension and rotation of the blade should be controlled and limited. Additionally, the blade's resting position should be within a secure housing, to eliminate the potential for accidental cutting or shearing. A desired instrument would alternately function as a dilating device when the cutting edge is in a resting position.

The present invention is intended to overcome one or more of the problems of the prior art devices discussed previously, and meet the requirements of a device suitable for extraction of pacemaker leads or other objects that may become embedded in biological tissue.

SUMMARY OF THE INVENTION

The present invention is a sheath-like instrument with a retractable, distal cutting blade which will track over and extract an object, such as a catheter or pacemaker lead, embedded in biological tissue, such as a blood vessel or heart chamber.

The present invention is simple in design and use and overcomes the disadvantages associated with the methods described above. The instrument consists of a slender sheath extended radially from a control handle. The sheath is rigid at the proximal end which is attached to the control handle, and flexible at the distal tip to allow precise placement of the distal tip next to the pacemaker lead or catheter. Disposed within the flexible, distal tip of the sheath is a cutting blade. The exertion of force (manually or motor driven) at the control handle causes the blade housed within the distal tip of the sheath to extend beyond the end of the sheath.

The cutting action of the blade involves concurrent, controlled rotation and blade extension, which provides a precise shearing action that separates the object from the biological tissue. The gentle combined slicing and dilating action of the instrument reduces the traction and countertraction forces required to separate the elongated object from tissue adhesions, thereby reducing the potential for tearing or rupturing the vessel wall or heart chamber. The coaxial design of this instrument allows it to track over the pacemaker lead keeping the blades parallel to the arterial walls thereby minimizing the risk of perforation due to perpendicular contact. By having a coaxial type blade, the instrument acts like a coring device, cutting tissue 360 degrees around the lead or item being extracted.

The distal tip of the instrument is sized and shaped so that while the blade is in a resting position, the tissue to be sheared is dilated, and separated as it encounters the extended blade. Blade extension only occurs when required, such as when the device encounters tissue adhesions, thus enhancing the safety of the procedure.

The flexible distal portion of the instrument in one embodiment is comprised of the metal bellows which supplies, in addition to flexibility, trackability and direct torque transfer to the distal cutting blade. The bellows also supplies spring action to facilitate blade extension.

DETAILED DESCRIPTION OF THE PREFERRED EMBODIMENTS

Figure 1:
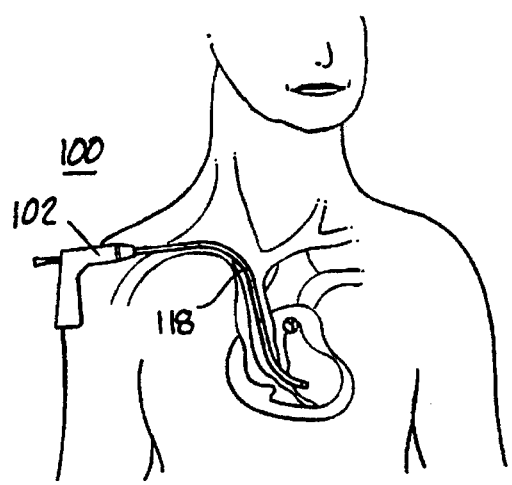
FIG. 1 is a perspective view of a human having a pacemaker lead located in the venous system and terminating electrode anchored to the ventricular heart chamber, with the mechanical lead removal apparatus of the present invention being shown inserted into the body and partly advanced over the lead.
Figure 2:
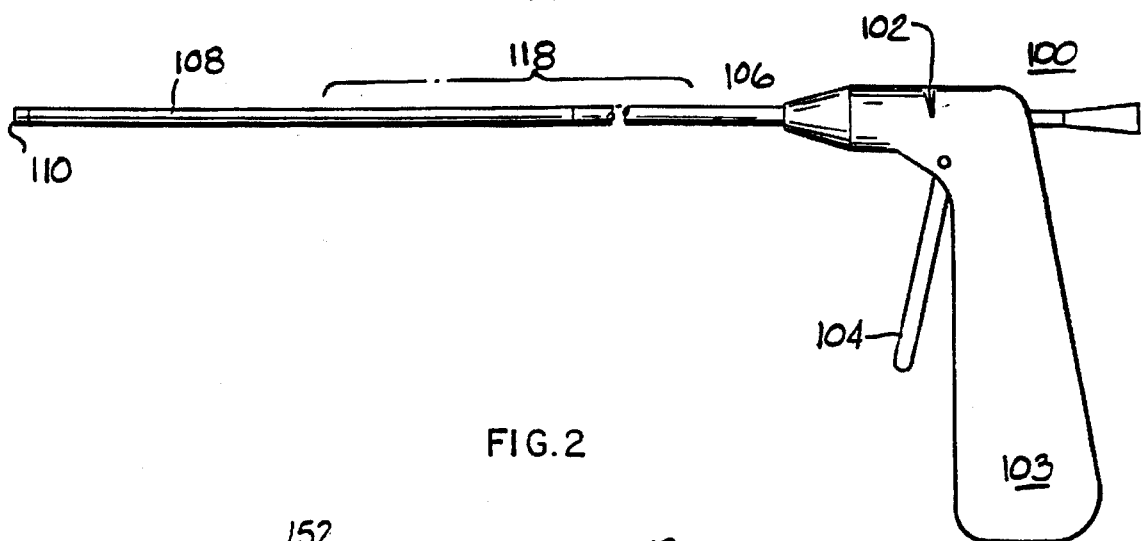
FIG. 2 is an elevational view of the mechanical lead removal apparatus of the present invention.

With reference to FIGS. 1 and 2, it can be seen that the apparatus of the invention 100 includes a control handle 102 extending radially from a long, slender sheath 118. The proximal end 106 of sheath 118 is rigid in construction while the distal end 108 of sheath 118 is generally flexible. Although it is understood that sheath 118 can vary in both length and diameter, in a preferred embodiment, sheath 118 is about 12" long, wherein the flexible distal portion 108 is about 6" long while the rigid proximal end 106 is 6" long. These dimensions optimally provide the control support for insertion of the device into the body while allowing for flexible yet controlled movement around curves. Generally, the diameter of sheath 118 is 3 mm, however it is understood that this may vary depending upon the particular application of the apparatus, and the object it is designed to remove. Note that the figures here are not drawn to scale and are intended primarily to provide an understanding of the device of the invention.

Sheath 118 is formed in a unitary fashion of a material suitable for insertion into the human body, and it houses a retractable blade and a bellows coupling system to control flexibility, all of which will subsequently be discussed.

Still with reference to FIG. 2, it can be seen that a control handle 102 is connected to and extends radially from sheath 118. Control handle 102 includes a grip 103 used to operate and control the device, and a trigger member 104 which is used to exert pressure through sheath 118, resulting in the extension of blade 114 beyond the distal tip 110 of sheath 118. Alternative embodiments of this pistol grip/trigger type handle include scissor type handles, rotary knobs, or other similar methods.

Housed within stationary outer sheath 118, is a tissue cutting apparatus including a hollow cylindrical cutting blade member 114 telescopically and rotatably mounted to a bellows assembly 126. The mechanism to control the rotational force applied to the bellows assembly 126 is contained within control handle 102. The mechanism is controlled manually, by either depression of trigger member 104, or alternatively by engaging a control switch or dial (not shown) located on control handle 102. This feature allows for blade extension to occur only when the operator is comfortable with the positioning of the instrument in relation to where the cut is to take place. Additionally, the amount of rotational force exerted may be motor driven or manual, through use of trigger member 104, thereby precisely controlling the cutting depth of the instrument. For example, one squeeze of the grip can provide 0.5 mm of cutting depth while ten squeezes of the grip can provide 5 mm of cutting depth.

Figure 3A:
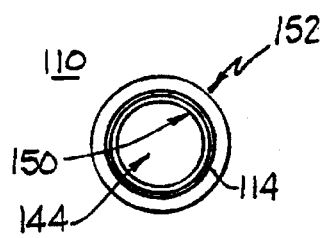
FIG. 3A is a front view of the distal tip of the device showing the inner lumen of the device and blade placement.
Figure 3:
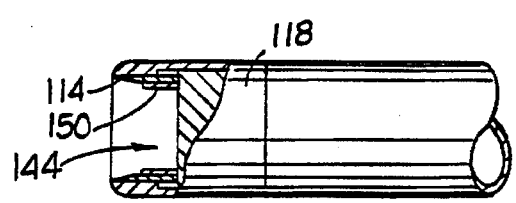
FIG. 3 is a side, partially cross-sectional view of the distal tip of the device shown in FIG. 2, with the blade retracted.
Figure 4:
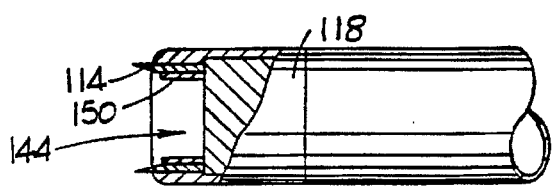
FIG. 4 is a side, partially cross-sectional view of the distal tip of the device shown in FIG. 2, with the blade extended.
Figure 5:
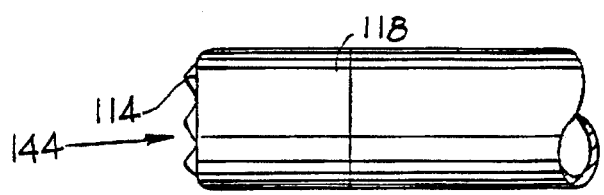
FIG. 5 is a side, side view of the distal tip of the device shown in FIG. 2, illustrating the blade configuration of the preferred embodiment.

Continuing now with FIGS. 3–5, which show cross-sectional views of the tip 110 of flexible distal portion 108 of sheath 118, the blade extension and retraction feature of the device is understood. FIG. 3 shows a cross-sectional view of tip 110, where blade 114 is disposed in a resting position. The blade 114 is fully encased within sheath 118 at all times that a rotational force is not being exerted by the operator. The distal tip 110 of sheath 118 has a blunt, non-traumatic leading edge that is circumferential in shape. While blade 114 is in a resting position, the distal tip 110 of sheath 118 acts as a dilating device, stretching tissue as it moves over the object to be extracted. (See also FIGS. 9–10 for a perspective view of the dilating action.)

FIG. 3A shows a front view of the blunt distal tip 110 of the device with the blade 114 disposed in a resting position. It can be seen that blade 114 rests between the inner radius 150 of the device 100 and the outer radius 152 of the device 100. Also seen with reference to FIG. 3A is the central lumen 144 which extends through the center of the device, all of which will subsequently be discussed.

FIG. 4 shows a cross-sectional view of the end 110 of sheath 118 with blade 114 extended. Here is can be seen that while the blunt leading edge stretches tissue, the blade 114 extends just beyond the distal tip 110 of sheath 118 when the operator makes contact with a tissue adhesion. As the blade is extended, a gentle stretching and slicing action takes place, and once complete, the blade 114 is retracted back within sheath 118 to its resting position.

Figure 6:
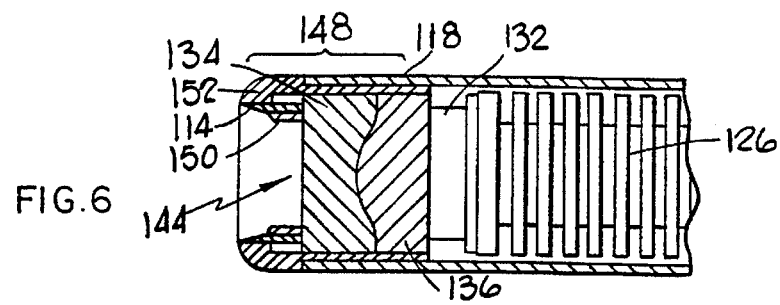
FIG. 6 is a partially cross-sectional view of the device shown in FIG. 2 illustrating the flexible bellows coupling system.
Figure 7:
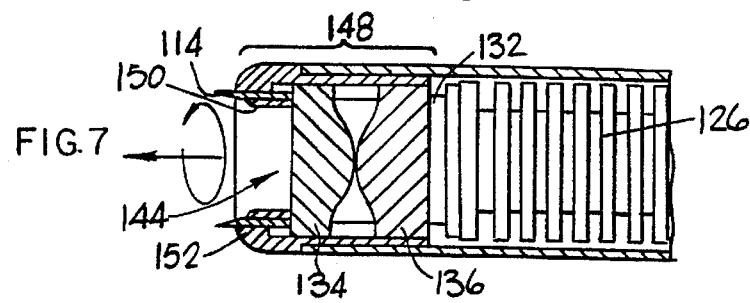
FIG. 7 is a partially cross-sectional view of the device shown in FIG. 2 illustrating the bellows and cam assembly exerting rotational force on the cutting blade.
Figure 8:
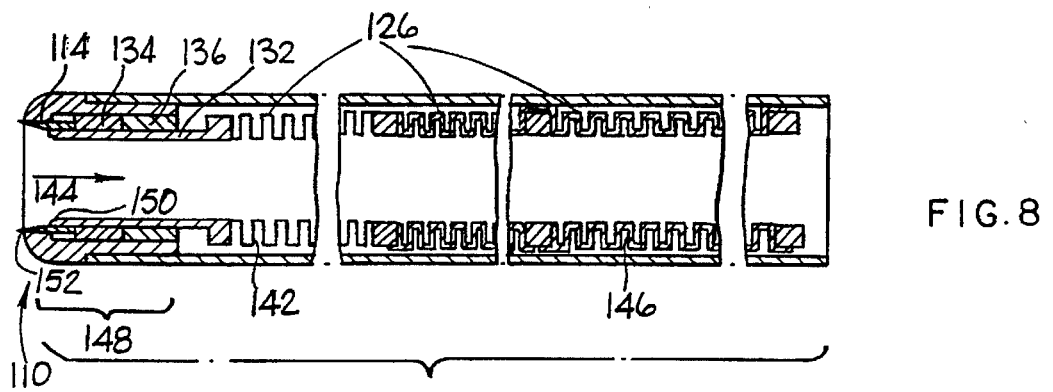
FIG. 8 is a side, cross-sectional side view of the bellows flexible coupling system shown in FIG. 6 illustrating alternative embodiments for the bellows flexible coupling system.

Continuing now with reference to FIGS. 6–8, which show a view side and cross-sectional views of the cam/bellow mechanism located within sheath 118, the flexible characteristics of the device and rotational force applied to the cutting instrument are readily understood. As seen in FIGS. 6–7, sheath 118 houses a cam/blade assembly 148 and a bellows coupling system 126 which extends longitudinally through the sheath 118. A central lumen 144 extends through the cam/blade assembly 148 and the bellows coupling system 126. One end of bellows coupling system 126 is in communication with a rotational mechanism housed within control handle 102. The other end of the bellows coupling system 126 is attached to the cam assembly 148. The bellows coupling system 126 functions as a flexible coupling system between the distal cutting instrument and the proximal rotation mechanism.

In one embodiment, the control handle 102 houses a conventional drive motor (not pictured). The drive includes an output shaft that can be rotated in a forward or reverse direction, depending on the action taken by the operator. Using either manual or motor driven force, rotation of the drive and the torsion that it provides are efficiently delivered to the cutting instrument through the flexible region provided by the bellows coupling system 126. Although the bellows assembly 126 is sufficiently flexible to accept curvature, it has a high degree is torsional stiffness, and thus provides good torque response. Torsion applied by the drive is transmitted to the distal tip 110 of the device immediately when the bellows coupling system 126 is rotated from its resting position, without any preloading of the flexible region prior to passing the torque to the distal cutting instrument 114. Also, the bellows assembly 126 does not expand in diameter by any significant amount as it rotates and applies torque to the distal tip 110, thereby reducing the possibility that the bellows coupling system 126 will bind within the sheath 118 during rotation.

The flexibility is a function of the width and number as well as the thickness of the bellows assembly 126. As seen with reference to FIG. 8, reference character 142 shows an example of the bellows assembly 126 for more flexibility, while reference character 146 shows a more rigid bellows assembly 126.

Although FIG. 8 is not drawn to scale, it is readily understood how the flexibility of sheath 118 increases from the proximal end 106 to the distal end 108 as the width, number and/or wall thickness of the bellows assembly 126 is increased or decreased.

Still with reference to FIGS. 6–8, it can be seen that the distal end 130 of the bellows assembly engages the cam/blade assembly 148 by bushing 132. FIG. 8, which depicts a cross-sectional view of the attachment, shows how the distal end of bellows coupling system 126 attaches to inner radius 150. The cam assembly 148 consists of a first cam 134 and a second cam 136. Inner radius 150 connects bushing 132 to the first cam 134. The second cam 136 is anchored to the outer housing of sheath 118, and allows bushing 132 to slide through it freely. As bellows assembly 126 is rotated in conjunction with bushing 132 and first cam 134, first cam 134 rotates against the fixed second cam 136, and the engagement of the respective cams causes the first cam 134 to extend outward, toward the tip 110 of sheath 118. Because blade 114 is fixed to first cam 134, blade 114 extends beyond the tip 110 of sheath 118, and cuts in a circumferential fashion. The circumferential nature of the cutting blade causes the instrument to act as a coring device, cutting tissue 360 degrees around the lead or item being extracted. Once the desired cut has been made, the operator releases the applied force. The bellows coupling system 126 is installed under a spring bias urging the first cam 134 against the second cam 136. Therefore, the release of the applied force allows the bellows to draw the first cam 134 back into the second cam 136.

There are several optional features that are not depicted in the drawings but easily understood as within the scope of the invention. For example, a wide variety of blade shapes and sizes may be used within this device. The blade may be extremely thin, and single edged, or it may be thick, or have a serrated edge (as seen with reference to FIG. 5). The size and shape of the blade will be dependent upon how the device is to be used.

Additionally, the force that is applied to the bellow/cam arrangement may be a manual force, created by the exertion of pressure by the operators finger on a trigger apparatus, or the force can be created by a motor contained within the control handle housing. The motor may be activated by the depression of an on/off switch.

Another feature that may be added to the present invention is a "tab" device or other means to indicate the extended or retracted position of the blade, and/or how far the blade has advanced beyond the sheath housing. Yet another feature that may be effected in accordance with the present invention is the possibility of saline or other fluid infusion to the spot where the cut is to be made. The saline or other liquids may be infused through a center tube disposed inside the lumen extending through the bellows coupling system. Additionally, an aspirator may be used in conjunction with this device. An aspiration tube may be inserted through the central chamber of sheath 118, and positioned at the place of the cutting blade 114.

Figure 9:
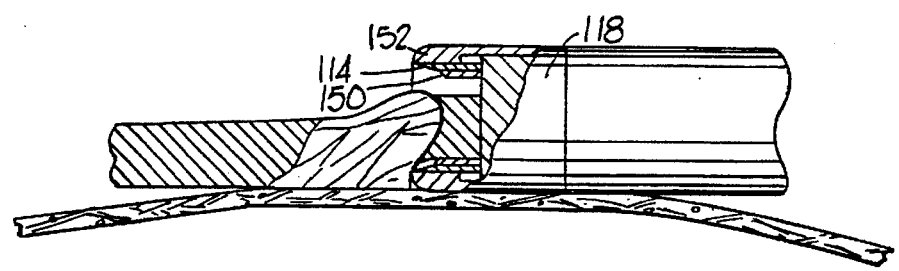
FIG. 9 is a side, partially cross-sectional view of the distal tip of the device in close proximity to a pacemaker lead partially covered with scar tissue, showing the operation of the device with the blade retracted.
Figure 10:
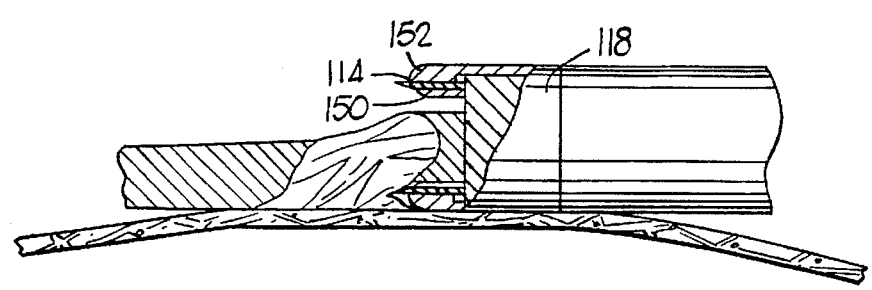
FIG. 10 is a side, partially cross-sectional view of the distal tip of the device in close proximity to a pacemaker lead partially covered with scar tissue, showing the combined stretching and shearing action of the device with the blade extended.

Use of the device is best understood with reference to FIGS. 1, 9 and 10. The operator of the device grasps the control handle 102 in one hand, and guides sheath 118 into the body of the person needing the surgery. The device is operated with one hand, freeing the other hand to provide traction on the pacing lead or object to be removed. The flexible distal portion 108 of sheath 118, bends and curves as the device is inserted into the body, to provide optimum placement of the distal tip 110 of sheath 118 around the pacemaker lead or the object.

As seen with reference to FIG. 9, while the blade 114 is retracted in the sheath 118, the instrument performs as a dilating sheath. The non-traumatic leading edge of distal tip 110 protects the vascular wall and the inner radius 150 keeps the blade 114 from coming in contact with insulation on the pacing lead. As the instrument is advanced, it stretches the scar tissue between the pacing lead and the vascular wall, thereby facilitating the shearing/cutting action of the instrument. The instrument tracks over the pacing lead keeping the blades parallel to the arterial walls, and minimizing the risk of perforation due to perpendicular contact.

With reference to FIG. 10, it can be seen that as the blade 114 is extended, the instrument is advanced while it gently shears the stretched scar tissue. Blade extension and rotation is precisely controlled by the exertion of pressure at the control handle. Once the adhesion site has been passed, the blade is retracted. Further traction is applied to the pacing lead at the proximal end of the instrument. The instrument is advanced to the next adhesion site and the progress of stretching, separating and shearing is repeated. Once the pacing lead is free from the vascular wall over its entire length, the lead may be pulled through the central lumen of the instrument and removed from the body.

I claim:

1. A surgical instrument that is constructed for inserting into a body, cutting tissue therein, and extracting an elongated object therefrom comprising:
    a flexible sheath including a sheath distal end opening, and a sheath hollow passageway positioned longitudinally in the sheath;
    a flexible elongated member rotatably positioned within the sheath hollow passageway, and an elongated hollow passageway positioned longitudinally therethrough for receiving the object; and
    a circumferential cutting instrument with a hole therethrough attached to the elongated member at the sheath distal end, the cutting instrument being rotatable and extendable in relation to the sheath by rotation of the elongated member.

2. The surgical instrument of claim 1, wherein the distal end opening is substantially circular in shape, with a blunt edge so that the sheath may stretch tissue as the sheath is disposed in the body.

3. The surgical instrument of claim 1, wherein the elongated member includes a set of bellows that are flexible in relation to a longitudinal axis but are rotationally rigid.

4. The surgical instrument of claim 1, further comprising a cam assembly with a first cam attached to the elongated member and a second cam attached to the sheath, the first and second cams being engaged with one another so that rotation of the elongated member in relation to the sheath urges the cutting instrument out of the distal end opening.

5. The surgical instrument of claim 4, wherein the first cam and second cam are annular in shape, the first cam is fixed to the cutting instrument and the first cam being positioned toward said distal end opening in relation to the second cam, the second cam having a central opening therethrough to receive the elongated member, the second cam allowing the elongated member to slide freely therethrough.

6. The surgical instrument of claim 5, wherein the elongated member is under a longitudinal tension urging the first cam toward the second cam.

7. A method of removing a pacemaker lead from a body comprising:
    inserting a free end of the lead into a hollow passageway of an elongated member, the elongated member being rotatably positioned within a hollow passageway of a sheath, and the elongated member having a distal end with a cutting instrument therein;

continuing to insert the lead into said elongated member hollow passageway so that the elongated member and sheath pass into the body, until stopped by an obstruction attaching the lead to the body;

concurrently extending and rotating the cutting instrument by rotating the elongated member in relation to the sheath to cut said obstruction.

8. The method of claim 7, wherein the cutting instrument is circumferential with a hole therethrough to receive the lead, and said rotating step includes extending the cutting instrument from the distal end.

9. The method of claim 8, wherein said extending step includes engaging a first annular cam attached to the elongated member with a second annular cam attached to the sheath.

* * * * *